(12) United States Patent
Klein et al.

(10) Patent No.: US 8,227,577 B2
(45) Date of Patent: Jul. 24, 2012

(54) BIVALENT, BISPECIFIC ANTIBODIES

(75) Inventors: Christian Klein, Iffeldorf (DE); Wolfgang Schaefer, Mannheim (DE)

(73) Assignee: Hoffman-La Roche Inc., Nutley, NJ (US)

( * ) Notice: Subject to any disclaimer, the term of this patent is extended or adjusted under 35 U.S.C. 154(b) by 249 days.

(21) Appl. No.: 12/332,531

(22) Filed: Dec. 11, 2008

(65) Prior Publication Data
US 2009/0175851 A1    Jul. 9, 2009

(30) Foreign Application Priority Data

Dec. 21, 2007   (EP) .................................. 07024866

(51) Int. Cl.
*C12P 21/08*       (2006.01)
*A61K 39/00*      (2006.01)
(52) U.S. Cl. ................. 530/387.3; 424/133.1; 424/136.1
(58) Field of Classification Search .................. None
See application file for complete search history.

(56) References Cited

U.S. PATENT DOCUMENTS 7,919,257 B2   4/2011  Hoogenboom et al.

FOREIGN PATENT DOCUMENTS

| WO | WO 99/37791 | 7/1999 |
|---|---|---|
| WO | 2006/093794 | 9/2006 |

OTHER PUBLICATIONS

Schoonjans, Willems, Schoonooghe, Fiers, Grooten and Mertens. Fab chains as an efficient heterodimerization scaffold for the production of recombinant bispecific and trispecific antibody derivatives. Journal of Immunology, 2000. vol. 165, pp. 7050-7057.*
Atwell, Ridgway, Wells, and Carter. Stable heterodimers from remodeling the domain interface of a homodimer using a phage display library. Journal of Molecular Biology, 1997. vol. 270, pp. 26-35.*
Merchant et al., Nature Biotech., 16, pp. 677-681 (1998).
Simon et al., The EMBO Journal, 9, pp. 1051-1056 (1990).
Morrison, S.L., Nature Biotech., 25, pp. 1233-1234 (2007).
Chan, L.A., et al., Variable Region Domain Exchange in Human IgGs Promotes Antibody Complex Formation with Accompanying Structural Changes and Altered Effector Functions; Molecular Immunology, 41 (2004) 527-538.
Morrison, S.L., et al , Variable Region Domain Exchange Influences the Functional Properties of IgG, Journal of Immunology 160 (1998) 2802-2808.

* cited by examiner

*Primary Examiner* — Anne M. Gussow
(74) *Attorney, Agent, or Firm* — George W. Johnston; Patricia S. Rocha-Tramaloni; Gene J. Yao

(57) ABSTRACT

The present invention relates to novel domain exchanged, bivalent, bispecific antibodies, their manufacture and use.

5 Claims, 9 Drawing Sheets

Antigen A

<IGF-1R> HC#
462 aa

VL-VH/CL-CH1 exchange <ANGPT2> HC##
467 aa

BIVALENT, BISPECIFIC ANTIBODIES

PRIORITY TO RELATED APPLICATION(S)

This application claims the benefit of European Patent Application No. 07024866.1, filed Dec. 21, 2007, which is hereby incorporated by reference in its entirety.

The present invention relates to novel bivalent, bispecific antibodies, their manufacture and use.

BACKGROUND OF THE INVENTION

Engineered proteins, such as bi- or multispecific antibodies capable of binding two or more antigens are known in the art. Such multispecific binding proteins can be generated using cell fusion, chemical conjugation, or recombinant DNA techniques.

A wide variety of recombinant bispecific antibody formats have been developed in the recent past, e.g. tetravalent bispecific antibodies by fusion of, e.g. an IgG antibody format and single chain domains (see e.g. Coloma, M. J., et al., Nature Biotech 15 (1997) 159-163; WO 2001/077342; and Morrison, S. L., Nature Biotech 25 (2007) 1233-1234).

Also several other new formats wherein the antibody core structure (IgA, IgD, IgE, IgG or IgM) is no longer retained such as dia-, tria- or tetrabodies, minibodies, several single chain formats (scFv, Bis-scFv), which are capable of binding two or more antigens, have been developed (Holliger, P., et al., Nature Biotech 23 (2005) 1126-1136 2005; Fischer, N., Léger, O., Pathobiology 74 (2007) 3-14; Shen, J-, et al., Journal of Immunological Methods 318 (2007) 65-74; Wu, C., et al., Nature Biotech 25 (2007) 1290-1297).

All such formats use linkers either to fuse the antibody core (IgA, IgD, IgE, IgG or IgM) to a further binding protein (e.g. scFv) or to fuse e.g. two Fab fragments or scFv. (Fischer, N., Léger, O., Pathobiology 74 (2007) 3-14). While it is obvious that linkers have advantages for the engineering of bispecific antibodies, they may also cause problems in therapeutic settings. Indeed, these foreign peptides might elicit an immune response against the linker itself or the junction between the protein and the linker. Further more, the flexible nature of these peptides makes them more prone to proteolytic cleavage, potentially leading to poor antibody stability, aggregation and increased immunogenicity. In addition one may want to retain effector functions, such as e.g. complement-dependent cytotoxicity (CDC) or antibody dependent cellular cytotoxicity (ADCC), which are mediated through the Fc receptor binding, by maintaining a high degree of similarity to naturally occurring.

Thus ideally, one should aim at developing bispecific antibodies that are very similar in general structure to naturally occurring antibodies (like IgA, IgD, IgE, IgG or IgM) with minimal deviation from human sequences.

In one approach bispecific antibodies that are very similar to natural antibodies have been produced using the quadroma technology (see Milstein, C., and Cuello, A. C., Nature 305 (1983) 537-40) based on the somatic fusion of two different hybridoma cell lines expressing murine monoclonal antibodies with the desired specificities of the bispecific antibody. Because of the random pairing of two different antibody heavy and light chains within the resulting hybrid-hybridoma (or quadroma) cell line, up to ten different antibody species are generated of which only one is the desired, functional bispecific antibody. Due to the presence of mispaired byproducts, and significantly reduced production yields, means sophisticated purification procedures are required (see e.g. Morrison, S. L., Nature Biotech 25 (2007) 1233-1234). In general the same problem of mispaired byproducts remains if recombinant expression techniques are used.

An approach to circumvent the problem of mispaired byproducts, which is known as 'knobs-into-holes', aims at forcing the pairing of two different antibody heavy chains by introducing mutations into the CH3 domains to modify the contact interface. On one chain bulky amino acids were replaced by amino acids with short side chains to create a 'hole'. Conversely, amino acids with large side chains were introduced into the other CH3 domain, to create a 'knob'. By coexpressing these two heavy chains (and two identical light chains, which have to be appropriate for both heavy chains), high yields of heterodimer formation ('knob-hole') versus homodimer formation ('hole-hole' or 'knob-knob') was observed (Ridgway, J. B., Presta, L. G., Carter, P. and WO 96/027011). The percentage of heterodimer could be further increased by remodeling the interaction surfaces of the two CH3 domains using a phage display approach and the introduction of a disulfide bridge to stabilize the heterodimers (Merchant, A. M, et al., Nature Biotech 16 (1998) 677-681; Atwell, S., Ridgway, J. B., Wells, J. A., Carter, P., J., Mol Biol 270 (1997) 26-35). New approaches for the knobs-into-holes technology are described in e.g. in EP 1870459A1. Although this format appears very attractive, no data describing progression towards the clinic are currently available. One important constraint of this strategy is that the light chains of the two parent antibodies have to be identical to prevent mispairing and formation of inactive molecules. Thus this technique is not appropriate for easily developing recombinant, bivalent, bispecific antibodies against two antigens starting from two antibodies against the first and the second antigen, as either the heavy chains of these antibodies an/or the identical light chains have to be optimized.

WO 99/37791 describes multipurpose antibody derivatives.

SUMMARY OF THE INVENTION

The invention relates to a bivalent, bispecific antibody, comprising:

a) the light chain and heavy chain of an antibody specifically binding to a first antigen,
wherein heavy chain domain CH3 of the antibody specifically binding to a first antigen is replaced by a constant heavy chain domain CH1;

b) the light chain and heavy chain of an antibody specifically binding to a second antigen,
wherein constant heavy chain domain CH3 of the antibody specifically binding to a second antigen is replaced by a constant light chain domain CL.

A further embodiment of the invention is a method for the preparation of an a bivalent, bispecific antibody according to the invention
comprising the steps of
a) transforming a host cell with
vectors comprising nucleic acid molecules encoding the light chain and heavy chain of an antibody specifically binding to a first antigen,
wherein heavy chain domain CH3 of the antibody specifically binding to a first antigen is replaced by a constant heavy chain domain CH1;
vectors comprising nucleic acid molecules encoding the light chain and heavy chain of an antibody specifically binding to a second antigen,
wherein constant heavy chain domain CH3 of the antibody specifically binding to a second antigen is replaced by a constant light chain domain CL;

b) culturing the host cell under conditions that allow synthesis of said antibody molecule; and c) recovering said antibody molecule from said culture.

A further embodiment of the invention is a host cell comprising vectors comprising nucleic acid molecules encoding the light chain and heavy chain of an antibody specifically binding to a first antigen, wherein the heavy chain domain CH3 of the antibody specifically binding to a first antigen is replaced by a constant heavy chain domain CH1; and vectors comprising nucleic acid molecules encoding the light chain and heavy chain of an antibody specifically binding to a second antigen, wherein constant heavy chain domain CH3 of the antibody specifically binding to a second antigen is replaced by a constant light chain domain CL.

A further embodiment of the invention is a composition, preferably a pharmaceutical or a diagnostic composition of the antibody according to the invention.

A further embodiment of the invention is a pharmaceutical composition comprising an antibody according to the invention and at least one pharmaceutically acceptable excipient.

A further embodiment of the invention is a method for the treatment of a patient in need of therapy, characterized by administering to the patient a therapeutically effective amount of an antibody according to the invention.

DETAILED DESCRIPTION OF THE INVENTION

The invention relates to a bivalent, bispecific antibody, comprising:
a) the light chain and heavy chain of an antibody specifically binding to a first antigen, wherein the heavy chain domain CH3 is replaced by a constant heavy chain domain CH1;
b) the light chain and heavy chain of an antibody specifically binding to a second antigen, wherein the constant heavy chain domain CH3 is replaced by a constant light chain domain CL.

Therefore said bivalent, bispecific antibody, comprises:
a) a first light chain and a first heavy chain of an antibody specifically binding to a first antigen, wherein the heavy chain domain CH3 is replaced by a constant heavy chain domain CH1;
b) a second light chain and a second heavy chain of an antibody specifically binding to a second antigen, wherein the constant heavy chain domain CH3 is replaced by a constant light chain domain CL.

The term "antibody" as used herein refers to whole, monoclonal antibodies. Such whole antibodies consist of two pairs of a "light chain" (LC) and a "heavy chain" (HC) (such light chain (LC)/heavy chain pairs are abbreviated herein as LC/HC). The light chains and heavy chains of such antibodies are polypeptides consisting of several domains. In a whole antibody, each heavy chain comprises a heavy chain variable region (abbreviated herein as HCVR or VH) and a heavy chain constant region. The heavy chain constant region comprises the heavy chain constant domains CH1, CH2 and CH3 (antibody classes IgA, IgD, and IgG) and optionally the heavy chain constant domain CH4 (antibody classes IgE and IgM). Each light chain comprises a light chain variable domain VL and a light chain constant domain CL. The structure of one naturally occurring whole antibody, the IgG antibody, is shown e.g. in FIG. 1. The variable domains VH and VL can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4 ((Janeway, C. A., Jr. et al. (2001). Immunobiology, 5th ed., Garland Publishing; and Woof, J., Burton, D., Nat Rev Immunol 4 (2004) 89-99). The two pairs of heavy chain and light chain (HC/LC) are capable of specifically binding to same antigen. Thus said whole antibody is a bivalent, monospecific antibody. Such "antibodies" include e.g. mouse antibodies, human antibodies, chimeric antibodies, humanized antibodies and genetically engineered antibodies (variant or mutant antibodies) as long as their characteristic properties are retained. Especially preferred are human or humanized antibodies, especially as recombinant human or humanized antibodies.

There are five types of mammalian antibody heavy chains denoted by the Greek letters: $\alpha$, $\delta$, $\epsilon$, $\gamma$ and $\mu$ (Janeway, C. A., Jr., et al., (2001). Immunobiology, 5th ed., Garland Publishing). The type of heavy chain present defines the class of antibody; these chains are found in IgA, IgD, IgE, IgG, and IgM antibodies, respectively (Rhoades, R. A., Pflanzer R G (2002). Human Physiology, 4th ed., Thomson Learning). Distinct heavy chains differ in size and composition; $\alpha$ and $\gamma$ contain approximately 450 amino acids, while $\mu$ and $\epsilon$ have approximately 550 amino acids.

Each heavy chain has two regions, the constant region and the variable region. The constant region is identical in all antibodies of the same isotype, but differs in antibodies of different isotype. Heavy chains $\gamma$, $\alpha$ and $\delta$ have a constant region composed of three constant domains CH1, CH2, and CH3 (in a line), and a hinge region for added flexibility (Woof, J., Burton, D., Nat Rev Immunol 4 (2004) 89-99); heavy chains $\mu$ and $\epsilon$ have a constant region composed of four constant domains CH1, CH2, CH3, and CH4 (Janeway, C. A., Jr., et al., (2001). Immunobiology, 5th ed., Garland Publishing). The variable region of the heavy chain differs in antibodies produced by different B cells, but is the same for all antibodies produced by a single B cell or B cell clone. The variable region of each heavy chain is approximately 110 amino acids long and is composed of a single antibody domain.

In mammals there are only two types of light chains, which are called lambda ($\lambda$) and kappa ($\kappa$). A light chain has two successive domains: one constant domain CL and one variable domain VL. The approximate length of a light chain is 211 to 217 amino acids.

The terms "monoclonal antibody" or "monoclonal antibody composition" as used herein refer to a preparation of antibody molecules of a single amino acid composition.

The "antibodies" according to the invention can be of any class (e.g. IgA, IgD, IgE, IgG, and IgM, preferably IgG or IgE), or subclass (e.g., IgG1, IgG2, IgG3, IgG4, IgA1 and IgA2, preferably IgG1), whereby both antibodies, from which the bivalent bispecific antibody according to the invention is derived, are of the same subclass (e.g. IgG1, IgG4 and the like, preferably IgG1), preferably of the same allotype (e.g. Caucasian).

A "Fc part of an antibody" is a term well known to the skilled artisan and defined on the basis of papain cleavage of antibodies. The antibodies according to the invention contain as Fc part, preferably a Fc part derived from human origin and preferably all other parts of the human constant regions. The Fc part of an antibody is directly involved in complement activation, C1q binding, C3 activation and Fc receptor binding. While the influence of an antibody on the complement system is dependent on certain conditions, binding to C1q is caused by defined binding sites in the Fc part. Such binding sites are known in the state of the art and described e.g. by Lukas, T. J., et al., J. Immunol. 127 (1981) 2555-2560; Brunhouse, R., and Cebra, J. J., Mol. Immunol. 16 (1979) 907-917; Burton, D. R., et al., Nature 288 (1980) 338-344; Thommesen, J. E., et al., Mol. Immunol. 37 (2000) 995-1004; Idusogie, E. E., et al., J. Immunol. 164 (2000) 4178-4184; Hezareh, M., et al., J. Virol. 75 (2001) 12161-12168; Morgan, A., et al., Immunology 86 (1995) 319-324; and EP 0307 434. Such binding sites are e.g. L234, L235, D270, N297, E318, K320, K322, P331 and P329 (numbering according to EU index of Kabat, see below). Antibodies of subclass IgG1, IgG2 and IgG3 usually show complement activation, C1q binding and C3 activation, whereas IgG4 do not activate the complement system, do not bind C1q and do not activate C3. Preferably the Fc part is a human Fc part.

The term "chimeric antibody" refers to an antibody comprising a variable region, i.e., binding region, from one source or species and at least a portion of a constant region derived from a different source or species, usually prepared by recombinant DNA techniques. Chimeric antibodies comprising a murine variable region and a human constant region are preferred. Other preferred forms of "chimeric antibodies" encompassed by the present invention are those in which the constant region has been modified or changed from that of the original antibody to generate the properties according to the invention, especially in regard to C1q binding and/or Fc receptor (FcR) binding. Such chimeric antibodies are also referred to as "class-switched antibodies." Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See, e.g., Morrison, S. L., et al., Proc. Natl. Acad. Sci. USA 81 (1984) 6851-6855; U.S. Pat. No. 5,202,238 and U.S. Pat. No. 5,204,244.

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." See, e.g., Riechmann, L., et al., Nature 332 (1988) 323-327; and Neuberger, M. S., et al., Nature 314 (1985) 268-270. Particularly preferred CDRs correspond to those representing sequences recognizing the antigens noted above for chimeric antibodies. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "human antibody", as used herein, is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Bruggemann, M., et al., Year Immunol. 7 (1993) 33-40). Human antibodies can also be produced in phage display libraries (Hoogenboom, H. R., and Winter, G., J. Mol. Biol. 227 (1992) 381-388; Marks, J. D., et al., J. Mol. Biol. 222 (1991) 581-597). The techniques of Cole, et al., and Boerner, et al. are also available for the preparation of human monoclonal antibodies (Cole, et al., Monoclonal Antibodies and Cancer Therapy, Alan R. Liss, p. 77 (1985); and Boerner, P., et al., J. Immunol. 147 (1991) 86-95). As already mentioned for chimeric and humanized antibodies according to the invention the term "human antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation.)

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

The "variable domain" (variable domain of a light chain (VL), variable region of a heavy chain (VH)) as used herein denotes each of the pair of light and heavy chains which is involved directly in binding the antibody to the antigen. The domains of variable human light and heavy chains have the same general structure and each domain comprises four framework (FR) regions whose sequences are widely conserved, connected by three "hypervariable regions" (or complementarity determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody heavy and light chain CDR3 regions play a particularly important role in the binding specificity/affinity of the antibodies according to the invention and therefore provide a further object of the invention.

The terms "hypervariable region" or "antigen-binding portion of an antibody" when used herein refer to the amino acid residues of an antibody which are responsible for antigen-binding. The hypervariable region comprises amino acid residues from the "complementarity determining regions" or "CDRs". "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. CDRs on each chain are separated by such framework amino acids. Especially, CDR3 of the heavy chain is the region which contributes most to antigen binding. CDR and FR regions are determined according to the standard definition of Kabat et al., Sequences of Proteins of Immunological Interest, 5th ed., Public Health Service, National Institutes of Health, Bethesda, Md. (1991).

The "constant domains" of the heavy chain and of the light chain are not involved directly in binding of an antibody to an antigen, but exhibit various effector functions. Depending on the amino acid sequence of the constant region of their heavy chains, antibodies or immunoglobulins are divided into the classes:

The term "bivalent, bispecific antibody" as used herein refers to an antibody as described above in which each of the two pairs of heavy chain and light chain (HC/LC) is specifically binding to a different antigen, i.e. the first heavy and the first light chain (originating from an antibody against a first antigen) are specifically binding together to a first antigen, and, the second heavy and the second light chain (originating from an antibody against a second antigen) are specifically binding together to a second antigen (as depicted in FIG. 2); such bivalent, bispecific antibodies are capable of specifically binding to two different antigens at the same time, and not to more than two antigens, in contrary to, on the one hand a monospecific antibody capable of binding only to one antigen, and on the other hand e.g. a tetravalent, tetraspecific antibody which can bind to four antigen molecules at the same time.

According to the invention, the ratio of a desired bivalent, bispecific antibody compared to undesired side products can be improved by the replacement of the CH3 domains of both heavy chains. Thus the heavy chain of an antibody specifically binding to a first antigen and the heavy chain of an antibody specifically binding to a second antigen are altered by the following replacement:

First heavy chain: replacement of the constant heavy chain domain CH3 by the constant heavy chain domain CH1 of said antibody specifically binding to a first antigen, and Second heavy chain: replacement of the constant heavy chain domain CH3 by the constant light chain domain CL of said antibody specifically binding to a second antigen.

Thus the resulting bivalent, bispecific antibodies are artificial antibodies which comprise
a) the light chain and heavy chain of an antibody specifically binding to a first antigen, wherein said heavy chain contains (at the position of the constant heavy chain domain CH3) a (second) constant heavy chain domain CH1 instead of the constant heavy chain domain CH3, and
b) the light chain and heavy chain of an antibody specifically binding to a second antigen, wherein said heavy chain contains a constant light chain domain CL instead of a constant heavy chain domain CH3.

The constant heavy chain domain CH1 by which the heavy chain domain CH3 is replaced can be of any Ig class (e.g. IgA, IgD, IgE, IgG, and IgM), or subclass (e.g., IgG1, IgG2, IgG3, IgG4, IgA1 and IgA2).

The constant light chain domain CL by which the heavy chain domain CH3 is replaced can be of the lambda ($\lambda$) or kappa ($\kappa$) type, preferably the kappa ($\kappa$) type.

In an additional aspect of the invention such improved ratio of a desired bivalent, bispecific antibody compared to undesired side products can be further improved by the additional alteration of the light chain and heavy chain of said antibody specifically binding to a second antigen according to one of the following three alternatives:

A) First Alternative (See FIG. 3):

The light chain and heavy chain of either said first antibody specifically binding to a first antigen or said second antibody specifically binding the second antigen is altered by the replacement of the variable domains VL and VH by each other.

or

B) Second Alternative (See FIG. 4):

The light chain and heavy chain of either said first antibody specifically binding to a first antigen or said second antibody specifically binding the second antigen is altered by the replacement of the constant domains CL and CH1 by each other.

or

C) Third Alternative (See FIG. 5):

The light chain and heavy chain of either said first antibody specifically binding to a first antigen or said second antibody specifically binding the second antigen is altered by the replacement of the variable domains VL and VH by each other, and by the replacement of the variable domains CL and CH1 by each other.

Thus one preferred embodiment of the invention is a bivalent, bispecific antibody, comprising:
a) the light chain and heavy chain of an antibody specifically binding to a first antigen, wherein the heavy chain domain CH3 is replaced by a constant heavy chain domain CH1;
b) the light chain and heavy chain of an antibody specifically binding to a second antigen, wherein the constant heavy chain domain CH3 is replaced by a constant light chain domain CL. and wherein optionally the light chain and heavy chain of either said first antibody specifically binding to a first antigen or said second antibody specifically binding the second antigen is altered
by the replacement of the variable domains VL and VH by each other,
and/or
by the replacement of the variable domains CL and CH1 by each other.

The terms "antigen" or "antigen molecule" as used herein are used interchangeable and refer to all molecules that can be specifically bound by an antibody. The bivalent, bispecific antibody is specifically binding to a first antigen and a second distinct antigen. The term "antigens" as used herein include e.g. proteins, different epitopes on proteins (as different antigens within the meaning of the invention), and polysaccharides. This mainly includes parts (coats, capsules, cell walls, flagella, fimbrae, and toxins) of bacteria, viruses, and other microorganisms. Lipids and nucleic acids are antigenic only when combined with proteins and polysaccharides. Non-microbial exogenous (non-self) antigens can include pollen, egg white, and proteins from transplanted tissues and organs or on the surface of transfused blood cells. Preferably the antigen is selected from the group consisting of cytokines, cell surface proteins, enzymes and receptors cytokines, cell surface proteins, enzymes and receptors.

Tumor antigens are those antigens that are presented by MHC I or MHC II molecules on the surface of tumor cells. These antigens can sometimes be presented by tumor cells and never by the normal ones. In this case, they are called tumor-specific antigens (TSAs) and typically result from a tumor specific mutation. More common are antigens that are presented by tumor cells and normal cells, and they are called tumor-associated antigens (TAAs). Cytotoxic T lymphocytes that recognized these antigens may be able to destroy the tumor cells before they proliferate or metastasize. Tumor antigens can also be on the surface of the tumor in the form of, for example, a mutated receptor, in which case they will be recognized by B cells.

In one preferred embodiment at least one of the two different antigens (first and second antigen), to which the bivalent, bispecific antibody specifically binds to, is a tumor antigen.

In another preferred embodiment both of the two different antigens (first and second antigen), to which the bivalent, bispecific antibody specifically binds to, are tumor antigens;

in this case the first and second antigen can also be two different epitopes at the same tumor specific protein.

In another preferred embodiment one of the two different antigens (first and second antigen), to which the bivalent, bispecific antibody specifically binds to, is a tumor antigen and the other is an effector cell antigen, as e.g. an T-Cell receptor, CD3, CD16 and the like.

In another preferred embodiment one of the two different antigens (first and second antigen), to which the bivalent, bispecific antibody specifically binds to, is a tumor antigen and the other is an anti-cancer substance such as a toxin or a kinase inhibitor.

As used herein, "specifically binding" or "binds specifically to" refers to an antibody specifically binding an antigen. Preferably the binding affinity of the antibody specifically binding this antigen is of KD-value of $10^{-9}$ mol/l or lower (e.g. $10^{-10}$ mol/l), preferably with a KD-value of $10^{-10}$ mol/l or lower (e.g. $10^{-12}$ mol/l). The binding affinity is determined with a standard binding assay, such as surface plasmon resonance technique (Biacore®).

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules.

An further embodiment of the invention is a method for the preparation of a bivalent, bispecific antibody according to the invention
comprising
a) transforming a host cell with
vectors comprising nucleic acid molecules encoding the light chain and heavy chain of an antibody specifically binding to a first antigen,
wherein the heavy chain domain CH3 is replaced by a constant heavy chain domain CH1;
vectors comprising nucleic acid molecules encoding the light chain and heavy chain of an antibody specifically binding to a second antigen,
wherein the constant heavy chain domain CH3 is replaced by a constant light chain domain CL;
b) culturing the host cell under conditions that allow synthesis of said antibody molecule; and
c) recovering said antibody molecule from said culture.

In general there are two vectors encoding the light chain and heavy chain of said antibody specifically binding to a first antigen, and further two vectors encoding the light chain and heavy chain of said antibody specifically binding to a second antigen. One of the two vectors is encoding the respective light chain and the other of the two vectors is encoding the respective heavy chain. However in an alternative method for the preparation of a bivalent, bispecific antibody according to the invention, only one first vector encoding the light chain and heavy chain of the antibody specifically binding to a first antigen and only one second vector encoding the light chain and heavy chain of the antibody specifically binding to a second antigen can be used for transforming the host cell.

The invention encompasses a method for the preparation of the antibodies comprising culturing the corresponding host cells under conditions that allow synthesis of said antibody molecules and recovering said antibodies from said culture, e.g. by expressing a first nucleic acid sequence encoding the light chain of an antibody specifically binding to a first antigen;
a second nucleic acid sequence encoding the heavy chain of said antibody specifically binding to a first antigen, wherein the heavy chain domain CH3 is replaced by a constant heavy chain domain CH1;
a third nucleic acid sequence encoding the light chain of an antibody specifically binding to a second antigen; and
a fourth nucleic acid sequence encoding the heavy chain of said antibody specifically binding to a second antigen, wherein the constant heavy chain domain CH3 is replaced by a constant light chain domain CL.

A further embodiment of the invention is a host cell comprising
vectors comprising nucleic acid molecules encoding the light chain and heavy chain of an antibody specifically binding to a first antigen,
wherein the heavy chain domain CH3 is replaced by a constant heavy chain domain CH1; and
vectors comprising nucleic acid molecules encoding the light chain and heavy chain of an antibody specifically binding to a second antigen,
wherein the constant heavy chain domain CH3 is replaced by a constant light chain domain CL.

A further embodiment of the invention is a host cell comprising
a) a vector comprising a nucleic acid molecule encoding the light chain and a vector comprising a nucleic acid molecule encoding the heavy chain, of an antibody specifically binding to a first antigen, wherein the heavy chain domain CH3 is replaced by a constant heavy chain domain CH1; and
b) a vector comprising a nucleic acid molecule encoding the light chain and a vector comprising a nucleic acid molecule encoding the heavy chain, of an antibody specifically binding to a second antigen, wherein the constant heavy chain domain CH3 is replaced by a constant light chain domain CL.

A further embodiment of the invention is a composition, preferably a pharmaceutical or a diagnostic composition of the bivalent, bispecific antibody according to the invention.

A further embodiment of the invention is a pharmaceutical composition comprising a bivalent, bispecific antibody according to the invention and at least one pharmaceutically acceptable excipient.

A further embodiment of the invention is a method for the treatment of a patient in need of therapy, characterized by administering to the patient a therapeutically effective amount of a bivalent, bispecific antibody according to the invention.

The term "nucleic acid or nucleic acid molecule", as used herein, is intended to include DNA molecules and RNA molecules. A nucleic acid molecule may be single-stranded or double-stranded, but preferably is double-stranded DNA.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

The term "transformation" as used herein refers to process of transfer of a vectors/nucleic acid into a host cell. If cells without formidable cell wall barriers are used as host cells, transfection is carried out e.g. by the calcium phosphate precipitation method as described by Graham, F. L., and van der Eb, A., J. Virology 52 (1978) 546-467. However, other methods for introducing DNA into cells such as by nuclear injection or by protoplast fusion may also be used. If prokaryotic cells or cells which contain substantial cell wall constructions are used, e.g. one method of transfection is calcium treatment using calcium chloride as described by Cohen, S., N, et al., PNAS. 69 (1972) 2110-2114.

Recombinant production of antibodies using transformation is well-known in the state of the art and described, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-161; Werner, R. G., et al., Arzneimittelforschung 48 (1998) 870-880 as well as in U.S. Pat. No. 6,331,415 and U.S. Pat. No. 4,816,567.

As used herein, "expression" refers to the process by which a nucleic acid is transcribed into mRNA and/or to the process by which the transcribed mRNA (also referred to as transcript) is subsequently being translated into peptides, polypeptides, or proteins. The transcripts and the encoded polypeptides are collectively referred to as gene product. If the polynucleotide is derived from genomic DNA, expression in a eukaryotic cell may include splicing of the mRNA.

A "vector" is a nucleic acid molecule, in particular self-replicating, which transfers an inserted nucleic acid molecule into and/or between host cells. The term includes vectors that function primarily for insertion of DNA or RNA into a cell (e.g., chromosomal integration), replication of vectors that function primarily for the replication of DNA or RNA, and expression vectors that function for transcription and/or translation of the DNA or RNA. Also included are vectors that provide more than one of the functions as described.

An "expression vector" is a polynucleotide which, when introduced into an appropriate host cell, can be transcribed and translated into a polypeptide. An "expression system" usually refers to a suitable host cell comprised of an expression vector that can function to yield a desired expression product.

The bivalent, bispecific antibodies according to the invention are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression, nucleic acids encoding light and heavy chains or fragments thereof are inserted into expression vectors by standard methods. Expression is performed in appropriate prokaryotic or eukaryotic host cells like CHO cells, NS0 cells, SP2/0 cells, HEK293 cells, COS cells, yeast, or E. coli cells, and the antibody is recovered from the cells (supernatant or cells after lysis). The bivalent, bispecific antibodies may be present in whole cells, in a cell lysate, or in a partially purified or substantially pure form. Purification is performed in order to eliminate other cellular components or other contaminants, e.g. other cellular nucleic acids or proteins, by standard techniques, including alkaline/SDS treatment, column chromatography and others well known in the art. See Ausubel, F., et al., ed., Current Protocols in Molecular Biology, Greene Publishing and Wiley Interscience, New York (1987).

Expression in NS0 cells is described by, e.g., Barnes, L. M., et al., Cytotechnology 32 (2000) 109-123; and Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; and Norderhaug, L., et al., J. Immunol. Methods 204 (1997) 77-87. A preferred transient expression system (HEK 293) is described by Schlaeger, E.-J., and Christensen, K., in Cytotechnology 30 (1999) 71-83 and by Schlaeger, E.-J., in J. Immunol. Methods 194 (1996) 191-199.

The control sequences that are suitable for prokaryotes, for example, include a promoter, optionally an operator sequence, and a ribosome binding site. Eukaryotic cells are known to utilize promoters, enhancers and polyadenylation signals.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

The bivalent, bispecific antibodies are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells such as HEK 293 cells, CHO cells, or myeloma cells that do not otherwise produce immunoglobulin protein, to obtain the synthesis of recombinant monoclonal antibodies in the host cells.

Amino acid sequence variants (or mutants) of the bivalent, bispecific antibody are prepared by introducing appropriate nucleotide changes into the antibody DNA, or by nucleotide synthesis. Such modifications can be performed, however, only in a very limited range, e.g. as described above. For example, the modifications do not alter the above mentioned antibody characteristics such as the IgG isotype and antigen binding, but may improve the yield of the recombinant production, protein stability or facilitate the purification.

The following examples, sequence listing and figures are provided to aid the understanding of the present invention, the true scope of which is set forth in the appended claims. It is understood that modifications can be made in the procedures set forth without departing from the spirit of the invention.

Sequence Listing

SEQ ID NO: 1 is the amino acid sequence of wild type <IGF-1R> antibody heavy chain SEQ ID NO: 2 is the amino acid sequence of wild type <IGF-1R> antibody light chain SEQ ID NO: 3 is the amino acid sequence of <IGF-1R> HC# antibody heavy chain#, wherein the heavy chain domain CH3 is replaced by a constant heavy chain domain CH1

SEQ ID NO: 4 is the amino acid sequence of wild type Angiopoietin-2 <ANGPT2> antibody heavy chain SEQ ID NO: 5 is the amino acid sequence of wild type Angiopoietin-2 <ANGPT2> antibody light chain SEQ ID NO: 6 is the amino acid sequence of the heavy chain* (HC*) of <ANGPT2> VL-VH/CL-CH1 exchange antibody, wherein the heavy chain domain VH is replaced by the light chain domain VL, and the heavy chain domain CH1 is replaced by the light chain domain CL based on SEQ ID NO: 4 and SEQ ID NO: 5.

SEQ ID NO: 7 is the amino acid sequence of the light chain* (LC*) of <ANGPT2> VL-VH/CL-CH1 exchange antibody, wherein the light chain domain VL is replaced by the heavy chain domain VH, and the light chain domain CL is replaced by the heavy chain domain CH1 based on SEQ ID NO: 4 and SEQ ID NO: 5.

SEQ ID NO: 8 is the amino acid sequence of VL-VH/CL-CH1 exchange <ANGPT2> HC## antibody heavy chain ##, wherein the heavy chain domain VH is replaced by the light chain domain VL, and the heavy chain domain CH1 is replaced by the light chain domain CL and wherein the constant heavy chain domain CH3 is replaced by a kappa constant light chain domain CL without a C-terminal Cysteine residue (including leader sequence)

SEQ ID NO: 9 is the amino acid sequence of VL-VH/CL-CH1 exchange <ANGPT2> HC## antibody heavy chain ##, wherein the heavy chain domain VH is replaced by the light chain domain VL, and the heavy chain domain CH1 is replaced by the light chain domain CL and wherein the constant heavy chain domain CH3 is replaced by a kappa constant light chain domain CL with a C-terminal Cysteine residue (including leader sequence); sequence corresponds to SEQ ID NO: 8

EXAMPLES

Materials & General Methods

Figure 1:
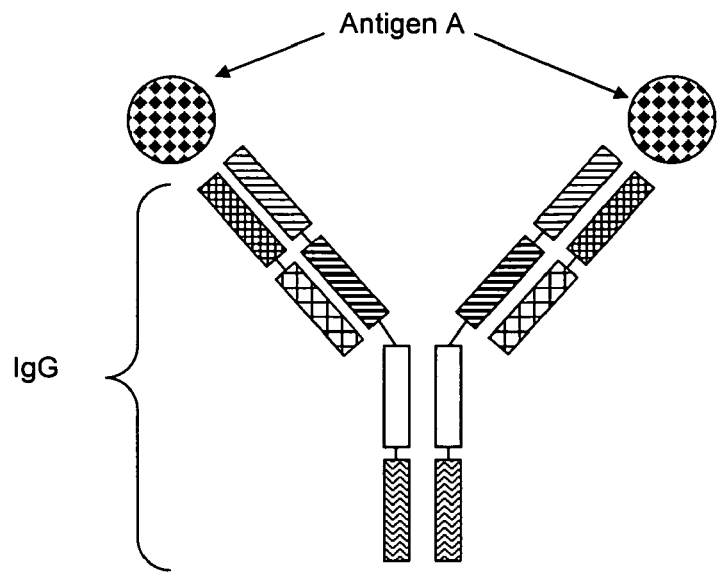
FIG. 1 Schematic figure of IgG, a naturally occurring whole antibody specific for one antigen with two pairs of heavy and light chain which comprise variable and constant domains in a typical order.
Figure 1:
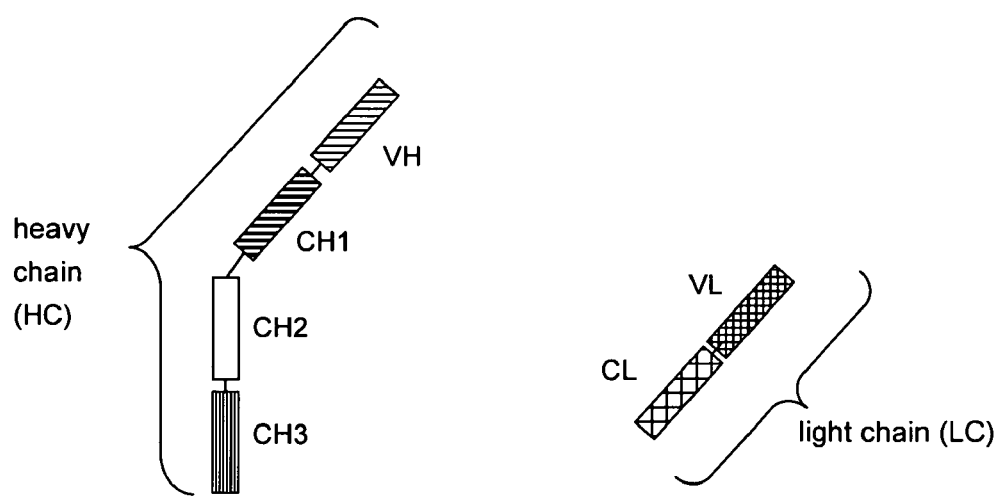
Figure 1:
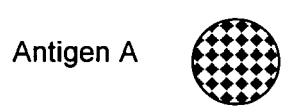
Figure 2:
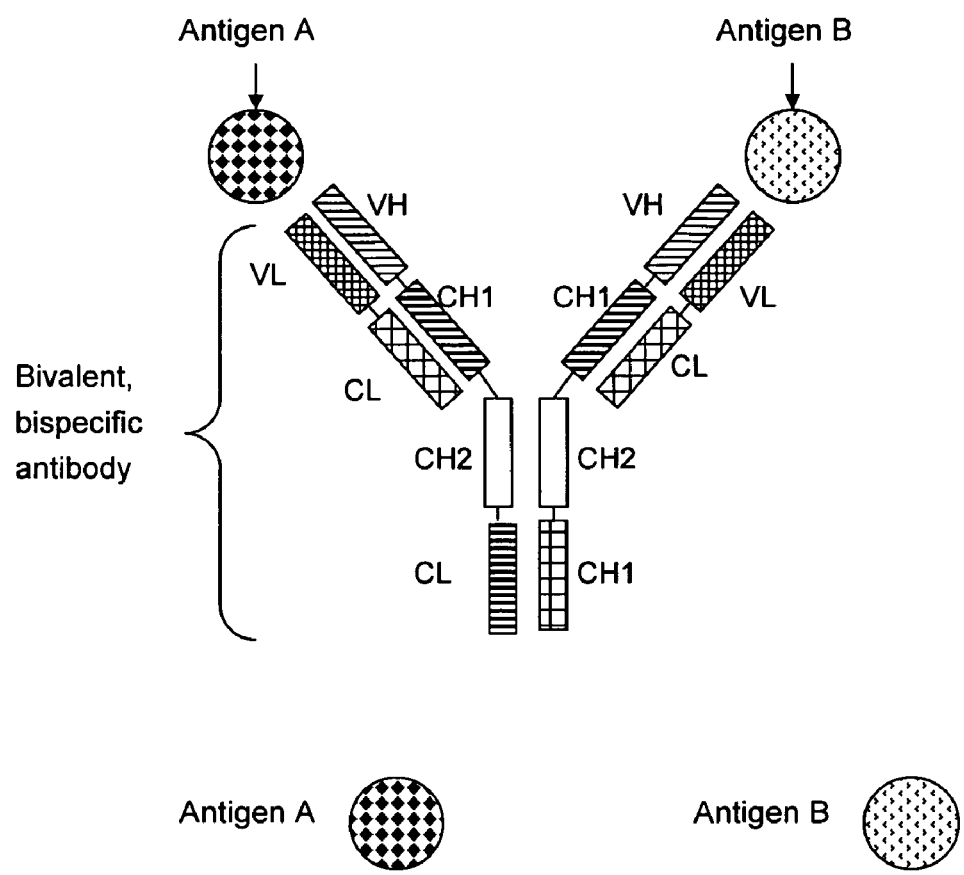
FIG. 2 Schematic figure of a bivalent, bispecific antibody, comprising: a) the light chain and heavy chain of an antibody specifically binding to a first antigen, wherein the heavy chain domain CH3 is replaced by a constant heavy chain domain CH1; b) the light chain and heavy chain of an antibody specifically binding to a second antigen, wherein the constant heavy chain domain CH3 is replaced by a constant light chain domain CL.
Figure 3:
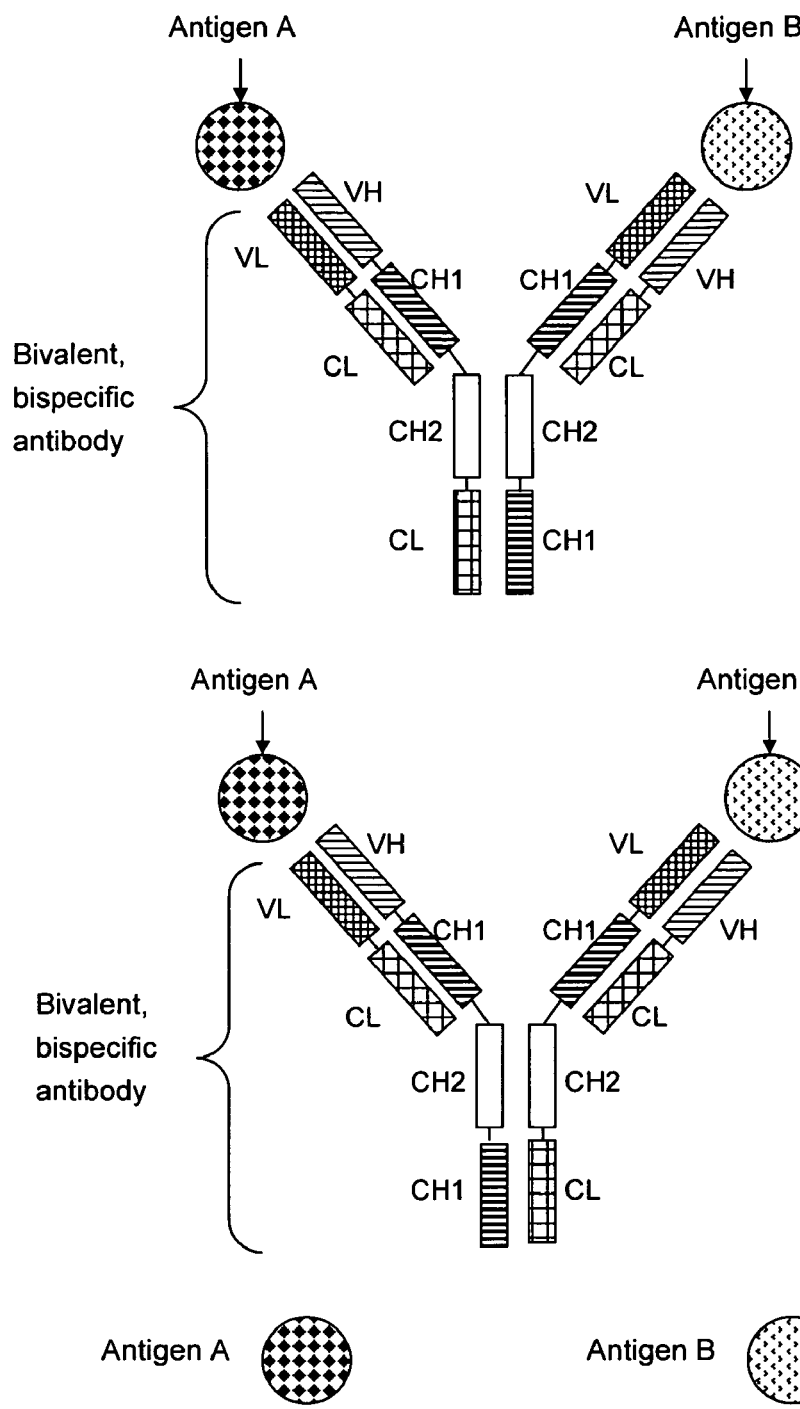
FIG. 3 Schematic figures of a bivalent, bispecific antibody, comprising: a) the light chain and heavy chain of an antibody specifically binding to a first antigen, wherein the heavy chain domain CH3 is replaced by a constant heavy chain domain CH1; b) the light chain and heavy chain of an antibody specifically binding to a second antigen, wherein the constant heavy chain domain CH3 is replaced by a constant light chain domain CL and wherein the light chain and heavy chain of either said first antibody specifically binding to a first antigen or said second antibody specifically binding the second antigen is altered by the replacement of the variable domains VL and VH by each other.
Figure 4:
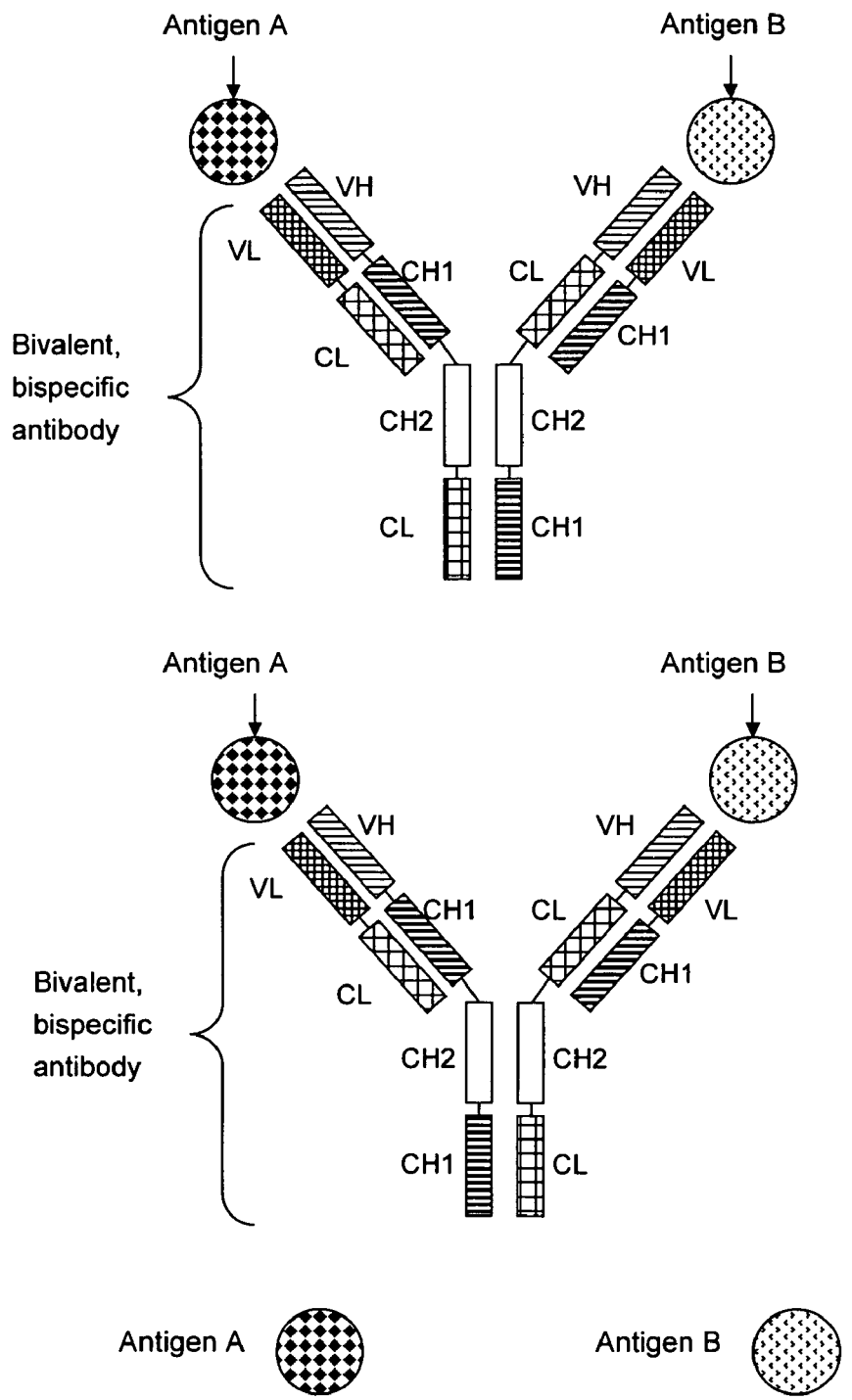
FIG. 4 Schematic figures of a bivalent, bispecific antibody, comprising: a) the light chain and heavy chain of an antibody specifically binding to a first antigen, wherein the heavy chain domain CH3 is replaced by a constant heavy chain domain CH1; b) the light chain and heavy chain of an antibody specifically binding to a second antigen, wherein the constant heavy chain domain CH3 is replaced by a constant light chain domain CL and wherein the light chain and heavy chain of either said first antibody specifically binding to a first antigen or said second antibody specifically binding the second antigen is altered by the replacement of the variable domains VL and VH by each other.

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, Md. (1991). Amino acids of antibody chains are numbered and referred to according to EU numbering (Edelman, G. M., et al., Proc. Natl. Acad. Sci. USA 63 (1969) 78-85; Kabat, E. A., et al., Sequences of Proteins of Immunological Interest, 5th ed., Public Health Service, National Institutes of Health, Bethesda, Md., (1991)).

Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.

Gene Synthesis

Desired gene segments were prepared from oligonucleotides made by chemical synthesis. The 600-1800 bp long gene segments, which are flanked by singular restriction endonuclease cleavage sites, were assembled by annealing and ligation of oligonucleotides including PCR amplification and subsequently cloned via the indicated restriction sites e.g. KpnI/SacI or AscI/PacI into a pPCRScript (Stratagene) based pGA4 cloning vector. The DNA sequences of the subcloned gene fragments were confirmed by DNA sequencing. Gene synthesis fragments were ordered according to given specifications at Geneart (Regensburg, Germany).

DNA Sequence Determination

DNA sequences were determined by double strand sequencing performed at MediGenomix GmbH (Martinsried, Germany) or Sequiserve GmbH (Vaterstetten, Germany).

DNA and Protein Sequence Analysis and Sequence Data Management

The GCG's (Genetics Computer Group, Madison, Wis.) software package version 10.2 and Infomax's Vector NT1 Advance suite version 8.0 was used for sequence creation, mapping, analysis, annotation and illustration.Expression vectors For the expression of the described antibodies variants of expression plasmids for transient expression (e.g. in HEK293 EBNA or HEK293-F) cells based either on a cDNA organization with a CMV-Intron A promoter or on a genomic organization with a CMV promoter were applied.

Beside the antibody expression cassette the vectors contained:

an origin of replication which allows replication of this plasmid in E. coli, and a β-lactamase gene which confers ampicillin resistance in E. coli.

The transcription unit of the antibody gene is composed of the following elements:

unique restriction site(s) at the 5' end the immediate early enhancer and promoter from the human cytomegalovirus, followed by the Intron A sequence in the case of the cDNA organization, a 5'-untranslated region of a human antibody gene, a immunoglobulin heavy chain signal sequence, the human antibody chain (wildtype or with domain exchange) either as cDNA or as genomic organization with an the immunoglobulin exon-intron organization a 3' untranslated region with a polyadenylation signal sequence, and unique restriction site(s) at the 3' end.

The fusion genes comprising the described antibody chains as described below were generated by PCR and/or gene synthesis and assembled with known recombinant methods and techniques by connection of the according nucleic acid segments e.g. using unique restriction sites in the respective vectors. The subcloned nucleic acid sequences were verified by DNA sequencing. For transient transfections larger quantities of the plasmids were prepared by plasmid preparation from transformed E. coli cultures (Nucleobond AX, Macherey-Nagel).

Cell Culture Techniques

Standard cell culture techniques were used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

Bispecific antibodies were expressed by transient co-transfection of the respective expression plasmids in adherently growing HEK293-EBNA or in HEK29-F cells growing in suspension as described below.

Transient Transfections in HEK293-EBNA System

Bispecific antibodies were expressed by transient co-transfection of the respective expression plasmids (e.g. encoding the heavy and modified heavy chain, as well as the corresponding light and modified light chain) in adherently growing HEK293-EBNA cells (human embryonic kidney cell line 293 expressing Epstein-Barr-Virus nuclear antigen; American type culture collection deposit number ATCC # CRL-10852, Lot. 959 218) cultivated in DMEM (Dulbecco's modified Eagle's medium, Gibco) supplemented with 10% Ultra Low IgG FCS (fetal calf serum, Gibco), 2 mM L-Glutamine (Gibco), and 250 μg/ml Geneticin (Gibco). For transfection FuGENE™ 6 Transfection Reagent (Roche Molecular Biochemicals) was used in a ratio of FuGENE™ reagent (μl) to DNA (μg) of 4:1 (ranging from 3:1 to 6:1). Proteins were expressed from the respective plasmids using a molar ratio of (modified and wildtype) light chain and heavy chain encoding plasmids of 1:1 (equimolar) ranging from 1:2 to 2:1, respectively. Cells were feeded at day 3 with L-Glutamine ad 4 mM, Glucose [Sigma] and NAA [Gibco]. Bispecific antibody containing cell culture supernatants were harvested from day 5 to 11 after transfection by centrifugation and stored at −20° C. General information regarding the recombinant expression of human immunoglobulins in e.g. HEK293 cells is given in: Meissner, P. et al., Biotechnol. Bioeng. 75 (2001) 197-203.

Transient Transfections in HEK293-F System

Bispecific antibodies were generated by transient transfection of the respective plasmids (e.g. encoding the heavy and modified heavy chain, as well as the corresponding light and modified light chain) using the HEK293-F system (Invitrogen) according to the manufacturer's instruction. Briefly, HEK293-F cells (Invitrogen) growing in suspension either in a shake flask or in a stirred fermenter in serumfree FreeStyle 293 expression medium (Invitrogen) were transfected with a mix of the four expression plasmids and 293fectin or fectin (Invitrogen). For 2 L shake flask (Corning) HEK293-F cells were seeded at a density of 1.0E*6 cells/mL in 600 mL and incubated at 120 rpm, 8% CO2. The day after the cells were transfected at a cell density of ca. 1.5E*6 cells/mL with ca. 42 mL mix of A) 20 mL Opti-MEM (Invitrogen) with 600 μg total plasmid DNA (1 μg/mL) encoding the heavy or modified heavy chain, respectively and the corresponding light chain in an equimolar ratio and B) 20 ml Opti-MEM+1.2 mL 293 fectin or fectin (2 μl/mL). According to the glucose consumption glucose solution was added during the course of the fermentation. The supernatant containing the secreted antibody was harvested after 5-10 days and antibodies were either directly purified from the supernatant or the supernatant was frozen and stored.

Protein Determination

The protein concentration of purified antibodies and derivatives was determined by determining the optical density (OD) at 280 nm, using the molar extinction coefficient calculated on the basis of the amino acid sequence according to Pace, C. N., et. al., Protein Science, 1995, 4, 2411-1423.

Antibody Concentration Determination in Supernatants

The concentration of antibodies and derivatives in cell culture supernatants was estimated by immunoprecipitation with Protein A Agarose-beads (Roche). 60 μL Protein A Agarose beads are washed three times in TBS-NP40 (50 mM Tris, pH 7.5, 150 mM NaCl, 1% Nonidet-P40). Subsequently, 1-15 mL cell culture supernatant were applied to the Protein A Agarose beads pre-equilibrated in TBS-NP40. After incubation for at 1 h at room temperature the beads were washed on an Ultrafree-MC-filter column (Amicon] once with 0.5 mL TBS-NP40, twice with 0.5 mL 2× phosphate buffered saline (2×PBS, Roche) and briefly four times with 0.5 mL 100 mM Na-citrate pH 5.0. Bound antibody was eluted by addition of 35 μl NuPAGE® LDS Sample Buffer (Invitrogen). Half of the sample was combined with NuPAGE® Sample Reducing Agent or left unreduced, respectively, and heated for 10 min at 70° C. Consequently, 5-30 μl were applied to an 4-12% NuPAGE® Bis-Tris SDS-PAGE (Invitrogen) (with MOPS buffer for non-reduced SDS-PAGE and MES buffer with NuPAGE® Antioxidant running buffer additive (Invitrogen) for reduced SDS-PAGE) and stained with Coomassie Blue.

The concentration of antibodies and derivatives in cell culture supernatants was quantitatively measured by affinity HPLC chromatography. Briefly, cell culture supernatants containing antibodies and derivatives that bind to Protein A were applied to an Applied Biosystems Poros A/20 column in 200 mM KH2PO4, 100 mM sodium citrate, pH 7.4 and eluted from the matrix with 200 mM NaCl, 100 mM citric acid, pH 2.5 on an Agilent HPLC 1100 system. The eluted protein was quantified by UV absorbance and integration of peak areas. A purified standard IgG1 antibody served as a standard.

Alternatively, the concentration of antibodies and derivatives in cell culture supernatants was measured by Sandwich-IgG-ELISA. Briefly, StreptaWell High Bind Strepatavidin A-96 well microtiter plates (Roche) were coated with 100 µL/well biotinylated anti-human IgG capture molecule F(ab')2<h-Fcγ>BI (Dianova) at 0.1 µg/mL for 1 h at room temperature or alternatively over night at 4° C. and subsequently washed three times with 200 µL/well PBS, 0.05% Tween (PBST, Sigma). 100 µL/well of a dilution series in PBS (Sigma) of the respective antibody containing cell culture supernatants was added to the wells and incubated for 1-2 h on a microtiterplate shaker at room temperature. The wells were washed three times with 200 µL/well PBST and bound antibody was detected with 100 µl F(ab')2<hFcγ>POD (Dianova) at 0.1 µg/mL as detection antibody for 1-2 h on a microtiterplate shaker at room temperature. Unbound detection antibody was washed away three times with 200 µL/well PBST and the bound detection antibody was detected by addition of 100 µL ABTS/well. Determination of absorbance was performed on a Tecan Fluor Spectrometer at a measurement wavelength of 405 nm (reference wavelength 492 nm).

Protein Purification

Proteins were purified from filtered cell culture supernatants referring to standard protocols. In brief, antibodies were applied to a Protein A Sepharose column (GE healthcare) and washed with PBS. Elution of antibodies was achieved at pH 2.8 followed by immediate neutralization of the sample. Aggregated protein was separated from monomeric antibodies by size exclusion chromatography (Superdex 200, GE Healthcare) in PBS or in 20 mM Histidine, 150 mM NaCl pH 6.0. Monomeric antibody fractions were pooled, concentrated if required using e.g. a MILLIPORE Amicon Ultra (30 MWCO) centrifugal concentrator, frozen and stored at −20° C. or −80° C. Part of the samples were provided for subsequent protein analytics and analytical characterization e.g. by SDS-PAGE, size exclusion chromatography or mass spectrometry.

SDS-PAGE

The NuPAGE® Pre-Cast gel system (Invitrogen) was used according to the manufacturer's instruction. In particular, 10% or 4-12% NuPAGE® Novex® Bis-TRIS Pre-Cast gels (pH 6.4) and a NuPAGE® MES (reduced gels, with NuPAGE® Antioxidant running buffer additive) or MOPS (non-reduced gels) running buffer was used.

Analytical Size Exclusion Chromatography

Size exclusion chromatography for the determination of the aggregation and oligomeric state of antibodies was performed by HPLC chromatography. Briefly, Protein A purified antibodies were applied to a Tosoh TSKgel G3000SW column in 300 mM NaCl, 50 mM KH2PO4/K2HPO4, pH 7.5 on an Agilent HPLC 1100 system or to a Superdex 200 column (GE Healthcare) in 2×PBS on a Dionex HPLC-System. The eluted protein was quantified by UV absorbance and integration of peak areas. BioRad Gel Filtration Standard 151-1901 served as a standard.

Mass Spectrometry

The total deglycosylated mass of crossover antibodies was determined and confirmed via electrospray ionization mass spectrometry (ESI-MS). Briefly, 100 µg purified antibodies were deglycosylated with 50 mU N-Glycosidase F (PNGaseF, ProZyme) in 100 mM KH2PO4/K2HPO4, pH 7 at 37° C. for 12-24 h at a protein concentration of up to 2 mg/ml and subsequently desalted via HPLC on a Sephadex G25 column (GE Healthcare). The mass of the respective heavy and light chains was determined by ESI-MS after deglycosylation and reduction. In brief, 50 µg antibody in 115 µl were incubated with 60 µl 1M TCEP and 50 µl 8 M Guanidin-hydrochloride subsequently desalted. The total mass and the mass of the reduced heavy and light chains was determined via ESI-MS on a Q-Star Elite MS system equipped with a NanoMate source.

Example 1

Production, Expression, Purification and Characterization of Bivalent, Bispecific <IGF-1R-ANGPT2> Antibody, Wherein in the Heavy Chain of the <IGF-1R> Antibody Part, the Heavy Chain Domain CH3 is Replaced by a Constant Heavy Chain Domain CH1, and Wherein in the Heavy Chain of the VL-VH/CL-CH1 Exchange <ANGPT2> Antibody, the Heavy Chain Domain CH3 is Replaced by a Kappa Constant Light Chain Domain Ck (Abbreviated Herein as <IGF-1R-ANGPT2> CH3-CH1/CH3-Ck Exchange Antibody)

Example 1A

Figure 5:
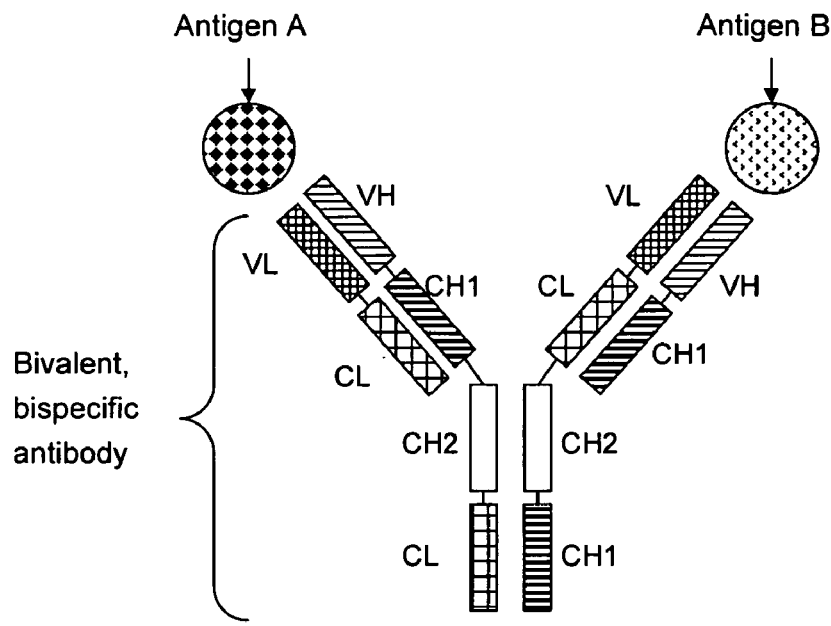
FIG. 5 Schematic figures of a bivalent, bispecific antibody, comprising: a) the light chain and heavy chain of an antibody specifically binding to a first antigen, wherein the heavy chain domain CH3 is replaced by a constant heavy chain domain CH1; b) the light chain and heavy chain of an antibody specifically binding to a second antigen, wherein the constant heavy chain domain CH3 is replaced by a constant light chain domain CL and wherein the light chain and heavy chain of either said first antibody specifically binding to a first antigen or said second antibody specifically binding the second antigen is altered by the replacement of the variable domains VL and VH by each other, and by the replacement of the variable domains VL and VH by each other.
Figure 5:
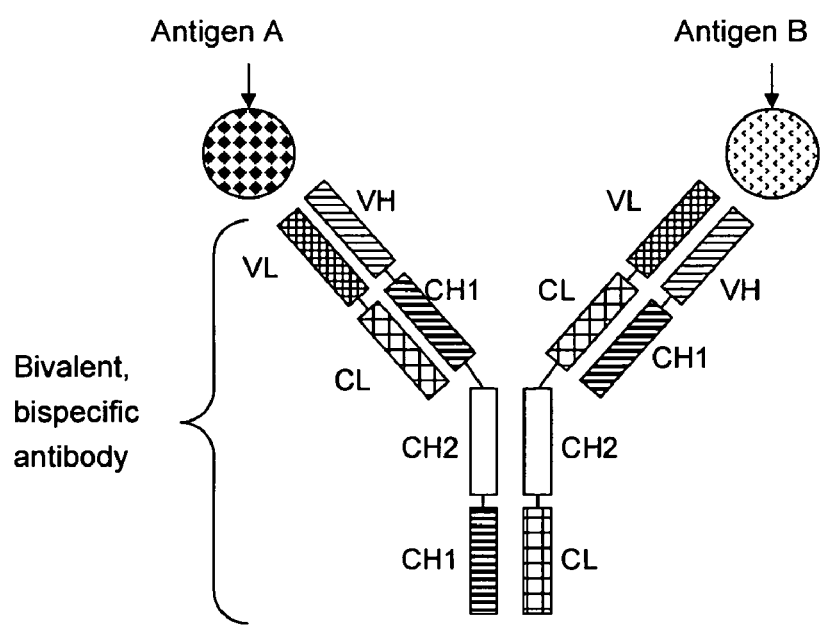
Figure 5:
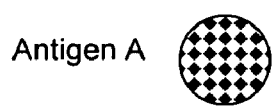
Figure 5:
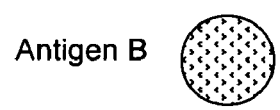

Making of the Expression Plasmids for the Modified Fc Region with CH1-Ck for CH3-CH3 Exchange In order to show that the CH1-Ck for CH3-CH3 exchange can be applied for the generation of bispecific antibodies via induction of heterodimerization of the respective Fc regions an antibody construct according to FIG. 5 was generated. For this sake plasmids for the co-expression of a wildtype <IGF-1R> antibody against IGF-1R and a VL-VH/CL-CH1 exchange <ANGPT2> antibody against Angiopoietin-2 were modified by exchange of the CH3 domain in the wildtype <IGF-1R> antibody with a CH1 domain and of the CH3 domain in the VL-VH/CL-CH1 exchange <ANGPT2> antibody with a CL (Ck) domain. The four corresponding plasmids were subsequently co-expressed and the generated antibody purified.

The sequence for the heavy variable domain including the respective leader sequence of the wildtype <IGF-1R> antibody heavy chain HC# with CH3-CH1 exchange was derived from a human <IGF-1R> antibody heavy chain (SEQ ID NO: 1) described in WO 2005/005635, and the heavy and light chain constant domains were derived from a human antibody (C-kappa and IgG1). The sequence for the wildtype <IGF-1R> antibody light chain LC (SEQ ID NO: 2) is described in WO 2005/005635.

In order to induce heterodimerization with a different heavy chain containing a CL (Ck) domain the gene segments encoding the <IGF-1R> antibody leader sequence, heavy chain variable domain (VH), heavy chain constant domain 1 (CH1), hinge and constant domain CH2 (VH-CH1-Hinge-CH2) were joined and fused to the 5'-end of a heavy chain constant domain 1 (CH1) instead of the heavy chain constant domain 3 (CH3). Linker sequences were optimized and differ from the natural sequences. The DNA coding for the respective fusion protein resulting from the exchange of the CH3 domain by the CH1 domain (CH3-CH1 exchange) was generated by gene synthesis and is denoted <IGF-1R> HC# (SEQ ID NO: 3) in the following.

The sequences for the heavy and light chain variable domains of the Angiopoietin-2 <ANGPT2> VL-VH/CL-CH1 exchange antibody including the respective leader sequences described in this example were derived from a human wildtype <ANGPT2> antibody heavy chain (SEQ ID NO: 4) and a light chain (SEQ ID NO: 5) described in WO 2006/045049 and the heavy and light chain constant domains were derived from a human antibody (C-kappa and IgG1). In order to obtain the respective <ANGPT2> VL-VH/CL-CH1 exchange antibody the following constructs were generated:

The gene segments encoding the <ANGPT2> antibody leader sequence, light chain variable domain (VL) and the human kappa-light chain constant domain (CL) were joined and fused to the 5'-end of the Fc domains of the human γ1-heavy chain constant domains (Hinge-CH2-CH3). The DNA coding for the respective fusion protein resulting from the exchange of VH and CH1 domains by VL and CL domains was generated by gene synthesis and is denoted VL-VH/CL-CH1 exchange <ANGPT2> HC* (heavy chain*) (SEQ ID NO: 6) in the following.

The gene segments for the <ANGPT2> antibody leader sequence, heavy chain variable domain (VH) and the human γ1-heavy chain constant domains (CH1) were joined as independent chain. The DNA coding for the respective fusion protein resulting from the exchange of VL and CL domains by VH and CH1 domains was generated by gene synthesis and is denoted VL-VH/CL-CH1 exchange <ANGPT2> LC* (light chain*) (SEQ ID NO: 7) in the following.

In order to induce heterodimerization with a second heavy chain containing a CH1 domain the sequence for the modified VL-VH/CL-CH1 exchange <ANGPT2> antibody heavy chain* HC* (SEQ ID NO: 6) was modified by the exchange of the CH3 domain by a Ck domain (CH3-Ck exchange). For this purpose. the gene segments encoding the <ANGPT2> antibody leader sequence, light chain variable domain (VL), light chain constant domain 1 (CL), hinge and constant domain CH2 (VL-CL-Hinge-CH2) from SEQ ID NO: 6 were joined and fused to the 5'-end of a kappa light chain constant domain (Ck) instead of the heavy chain constant domain 3 (CH3). Linker sequences were optimized and differ from the natural sequences. Two sequences were evaluated either ending without a C-terminal cysteine (SEQ ID NO: 8) or ending with a C-terminal cysteine (SEQ ID NO: 9). The DNA coding for the respective fusion protein resulting from the exchange of the CH3 domain by the kappa CL domain (CH3-Ck exchange) was generated by gene synthesis and was denoted <ANGPT2> HC## (SEQ IDs NO: 8 and NO:9) in the following.

Figure 6:
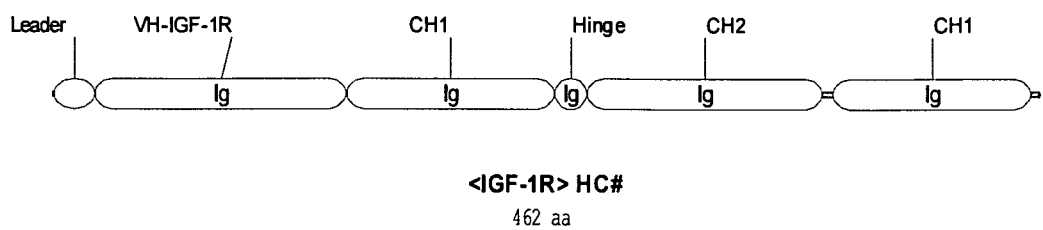
FIG. 6 Protein sequence scheme of CH1-CL for CH3-CH3 exchange <IGF-1R> HC#
Figure 7:
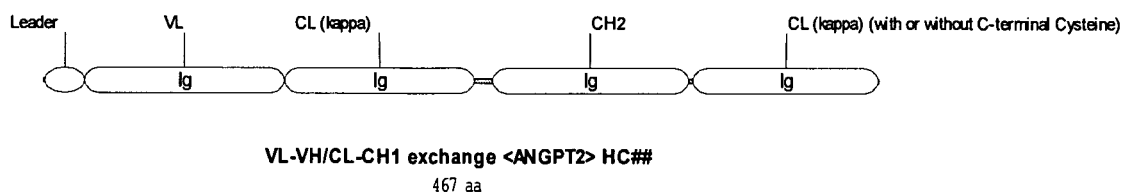
FIG. 7 Protein sequence scheme of CH1-CL for CH3-CH3 exchange <ANGPT2> HC## (with a kappa constant light chain domain CL)
Figure 8:
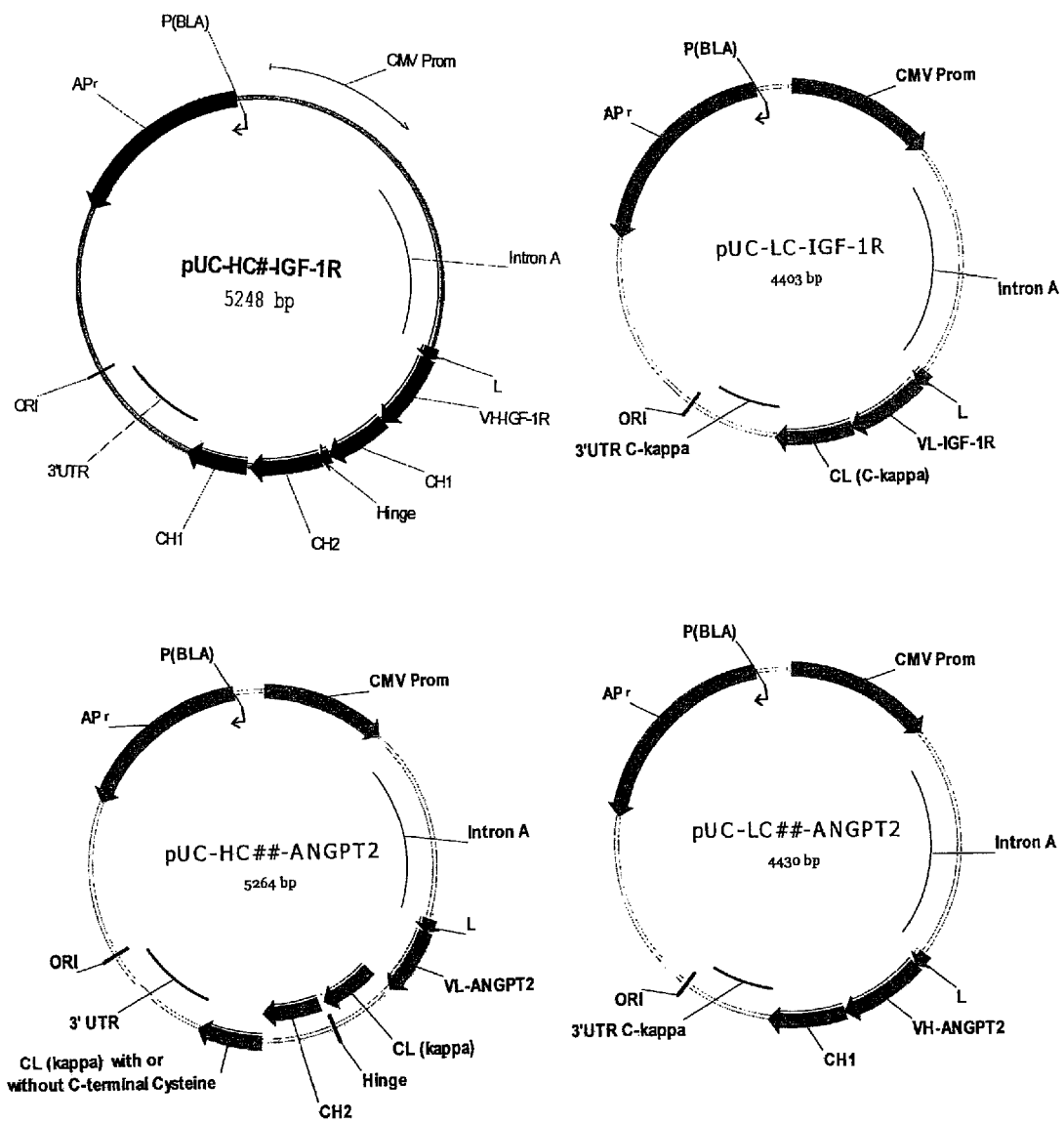
FIG. 8 Plasmid maps of CH1-Ck for CH3-CH3 exchange <IGF-1R> HC# expression vector pUC-HC#-IGF-1R and the respective pUC <IGF-1R> LC expression vector pUC-LC-IGF-1R and of CH1-Ck for CH3-CH3 exchange <ANGPT2> VL-VH/CL-CH1 exchange HC## expression vector pUC-HC##-ANGPT2 and the respective <ANGPT2> VL-VH/CL-CH1 exchange LC expression vector pUC-LC##-ANGPT2

FIG. 6 and FIG. 7 show a schematic view of the protein sequence of the modified <IGF-1R> heavy chain HC# and the modified VL-VH/CL-CH1 exchange <ANGPT2> antibody heavy chain HC## with or without the C-terminal Cysteine responsible for the heterodimerization of the respective bispecific antibodies. FIG. 8 shows an overview of the applied 4 vectors to generate bispecific antibodies (4-vector system).

Example 1B

Figure 9:
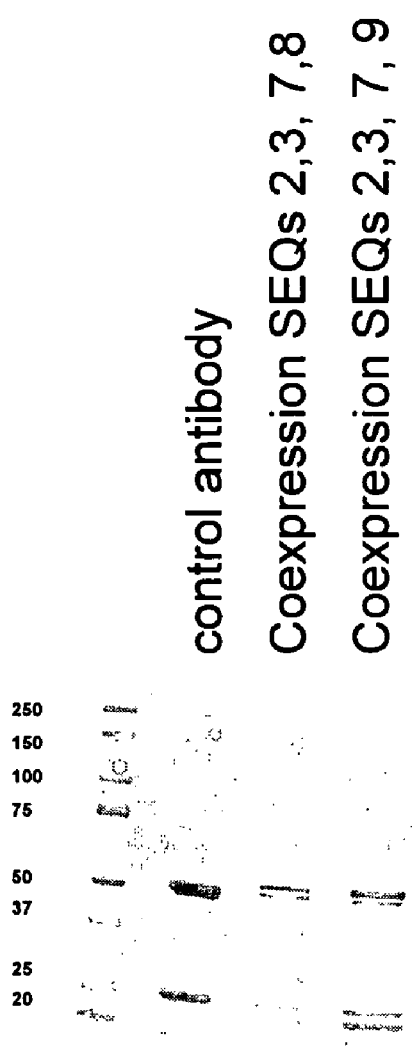
FIG. 9 SDS-PAGE of co-expression of plasmids pUC-HC#-IGF-1R and pUC-HC##-ANGPT2 together with the respective light chain vectors for the <IGF-1R> wildtype light chain (SEQ ID NO: 2) and the VL-VH/CL-CH1 exchange <ANGPT2> light chain (SEQ ID NO: 8) using the HEK293-F system.

Transient Expression and Purification of the Bispecific <IGF-1R-ANGPT2> CH3-CH1/CH3-Ck Exchange Antibody with Modified Fc Region In the following, the four plasmids coding for the modified <IGF-1R> heavy chain HC# (pUC-HC#-IGF-1R) (SEQ ID NO: 3) and for the modified VL-VH/CL-CH1 exchange <ANGPT2> antibody heavy chain HC## (pUC-HC##-ANGPT2) (either SEQ ID NO: 8 without Cysteine residue or SEQ ID NO: 9 with Cysteine residue) were transiently co-expressed at equimolar ratios together with the respective light chain vectors for the <IGF-1R> wildtype light chain LC (pUC-LC-IGF-1R) (SEQ ID NO: 2) and the modified VL-VH/CL-CH1 exchange <ANGPT2> antibody light chain LC* (pUC-LC*-ANGPT2) (SEQ ID: 7), respectively as described above (FIG. 8). Bispecific antibodies were subsequently purified via Protein A followed by size exclusion chromatography as described above. FIG. 9 shows the SDS-PAGE of the purified protein from the two expressions either with the plasmid coding for the modified VL-VH/CL-CH1 exchange <ANGPT2> antibody heavy chain HC## either without or with the C-terminal Cysteine. The SDS-PAGE indicated that in the purified antibodies indeed 4 different protein chains from the desired functional bispecific <IGF-1R-ANGPT2> CH3-CH1/CH3-Ck exchange antibody were present in similar ratios.

Example 1E

Figure 10:
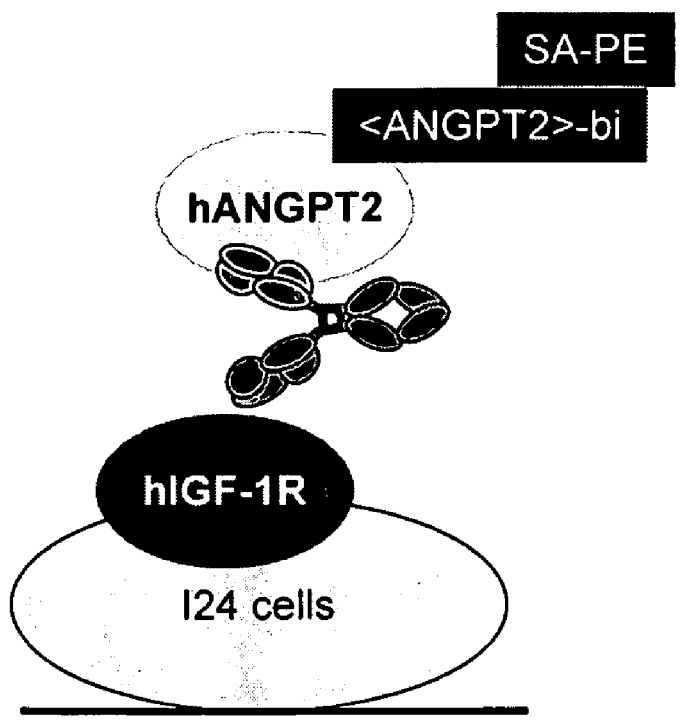
FIG. 10 Assay principle of cellular FACS IGF-1R-ANGPT2 bridging assay on I24 IGF-1R expressing cells to detect the presence of functional bispecific <ANGPT2-IGF-1R> VL-VH exchange antibody

Detection of Functional Bispecific <IGF-1R-ANGPT2> CH3-CH1/CH3-Ck Exchange Antibodies with Modified Fc Region with CH3-CH1/CH3-Ck Exchange in a Cellular FACS Bridging Assay on I24 IGF-1R Expressing Cells In order to confirm the presence of functional bispecific <IGF-1R-ANGPT2> CH3-CH1/CH3-Ck exchange antibodies with modified Fc region with CH1-Ck for CH3-CH3 exchange a cellular FACS IGF-1R-ANGPT2 bridging assay on I24 cells (NIH3T3 cells expressing recombinant human IGF-1R, Roche) is performed. The assay principle is depicted in FIG. 10. A bispecific <IGF-1R-ANGPT2> that is present in the purified antibody mix, respectively; is capable of binding to IGF-1R in I24 cells and to ANGPT2 simultaneously; and thus will bridge its two target antigens with the two opposed Fab regions.

Briefly, 5×10E5 I24 cells per FACS tube are incubated with total purified antibody mix and incubated on ice for 1 h. The respective purified antibody is applied to the I24 cells. Unbound antibody is washed away with 4 ml ice cold PBS (Gibco)+2% FCS (Gibco), cells are centrifuged (5 min at 400 g) and bound bispecific antibody is detected with 50 µl 2 µg/mL human Angiopoietin-2 (R&D Systems) for 1 h on ice. Subsequently, unbound Angiopoietin-2 is washed away once or twice with 4 ml ice cold PBS (Gibco)+2% FCS (Gibco), cells are centrifuged (5 min at 400 g) and bound Angiopoietin-2 is detected with 50 µl 5 µg/mL <Ang-2>mIgG1-Biotin antibody (BAM0981, R&D Systems) for 45 min on ice; alternatively, cells are incubated with 50 µg 5 µg/mL mIgG1-Biotin-Isotype control (R&D Systems). Unbound detection antibody is washed away with 4 ml ice cold PBS (Gibco)+2% FCS (Gibco), cells are centrifuged (5 min at 400 g) and bound detection antibody is detected with 50 µl 1:400 Streptavidin-PE conjugate (Invitrogen/Zymed) for 45 min on ice protected from light. Unbound Streptavidin-PE conjugate is washed away with 4 ml ice cold PBS+2% FCS. Subsequently, cells are centrifuged (5 min 400 g), resuspended in 300-500 µL PBS and bound Streptavidin-PE conjugate is quantified on a FACSCalibur or FACS Canto (BD (FL2 channel, 10,000 cells per acquisition). During the experiment the respective isotype controls are included to exclude any unspecific binding events. In addition, purified monospecific, bivalent IgG1 antibodies <IGF-1R> and <ANGPT2> are included as controls.

The invention claimed is:

1. A bivalent, bispecific antibody, comprising:
   a) the light chain and heavy chain of an antibody specifically binding to a first antigen, wherein heavy chain domain CH3 of the antibody specifically binding to a first antigen is replaced by a constant heavy chain domain CH1; and
   b) the light chain and heavy chain of an antibody specifically binding to a second antigen, wherein constant heavy chain domain CH3 of the antibody specifically binding to a second antigen is replaced by a constant light chain domain CL.

2. The antibody according to claim 1, wherein the light chain and heavy chain of either of the first antibody specifically binding to a first antigen or said second antibody specifically binding the second antigen is altered by one or both of (1) the replacement of the variable domains VL and VH by each other and (2) the replacement of the variable domains CL and CH1 by each other.

3. A method for the preparation of a bivalent, bispecific antibody according to claim 1 comprising the steps of a) transforming a host cell with
   vectors comprising nucleic acid molecules encoding the light chain and heavy chain of an antibody specifically binding to a first antigen, wherein heavy chain domain CH3 of the antibody specifically binding to a first antigen is replaced by a constant heavy chain domain CH1; and
   vectors comprising nucleic acid molecules encoding the light chain and heavy chain of an antibody specifically binding to a second antigen, wherein constant heavy chain domain CH3 of the antibody specifically binding to a second antigen is replaced by a constant light chain domain CL;
b) culturing the host cell under conditions that allow synthesis of said antibody molecule; and
c) recovering said antibody molecule from said culture.

4. A composition comprising a bivalent, bispecific antibody according to claim 1 and at least one pharmaceutically acceptable excipient.

5. A composition comprising a bivalent, bispecific antibody according to claim 2 and at least one pharmaceutically acceptable excipient.

* * * * *

UNITED STATES PATENT AND TRADEMARK OFFICE
CERTIFICATE OF CORRECTION

PATENT NO.         : 8,227,577 B2
APPLICATION NO.    : 12/332531
DATED              : July 24, 2012
INVENTOR(S)        : Klein et al.

It is certified that error appears in the above-identified patent and that said Letters Patent is hereby corrected as shown below:

On the Title Page, under Item (73) Assignee:

Delete "Hoffman-La Roche Inc., Nutley, NJ (US)"

And insert -- Hoffmann-La Roche Inc., Nutley, NJ (US) --

Signed and Sealed this
Second Day of October, 2012

David J. Kappos
*Director of the United States Patent and Trademark Office*

SEQUENCE LISTING

<160> NUMBER OF SEQ ID NOS: 9

<210> SEQ ID NO 1
<211> LENGTH: 467
<212> TYPE: PRT
<213> ORGANISM: Homo sapiens

<400> SEQUENCE: 1

Met Glu Phe Gly Leu Ser Trp Val Phe Leu Val Ala Leu Leu Arg Gly
1               5                   10                  15

Val Gln Cys Gln Val Glu Leu Val Glu Ser Gly Gly Gly Val Val Gln
            20                  25                  30

Pro Gly Arg Ser Gln Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Ile Ile Trp Phe Asp Gly Ser Ser Thr Tyr Tyr Ala
65                  70                  75                  80

Asp Ser Val Arg Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Phe Cys Ala Arg Glu Leu Gly Arg Arg Tyr Phe Asp Leu Trp Gly
        115                 120                 125

Arg Gly Thr Leu Val Ser Val Ser Ser Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

-continued

Tyr Thr Leu Pro Pro Ser Arg Asp Glu Leu Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 2
<211> LENGTH: 235
<212> TYPE: PRT
<213> ORGANISM: Homo sapiens

<400> SEQUENCE: 2

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Lys Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Lys Trp Pro Pro Trp Thr Phe Gly Gln Gly Thr Lys Val Glu Ser Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 3
<211> LENGTH: 462
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 3

```
Met Glu Phe Gly Leu Ser Trp Val Phe Leu Val Ala Leu Leu Arg Gly
1               5                   10                  15

Val Gln Cys Gln Val Glu Leu Val Glu Ser Gly Gly Gly Val Val Gln
            20                  25                  30

Pro Gly Arg Ser Gln Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Ile Ile Trp Phe Asp Gly Ser Ser Thr Tyr Tyr Ala
65                  70                  75                  80

Asp Ser Val Arg Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Phe Cys Ala Arg Glu Leu Gly Arg Arg Tyr Phe Asp Leu Trp Gly
        115                 120                 125

Arg Gly Thr Leu Val Ser Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Ala Ala Pro Ser Val
        355                 360                 365

Phe Pro Leu Ala Pro Ser Ser Lys Ser Thr Ser Gly Gly Thr Ala Ala
    370                 375                 380

Leu Gly Cys Leu Val Lys Asp Tyr Phe Pro Glu Pro Val Thr Val Ser
385                 390                 395                 400
```

```
Trp Asn Ser Gly Ala Leu Thr Ser Gly Val His Thr Phe Pro Ala Val
                405                 410                 415

Leu Gln Ser Ser Gly Leu Tyr Ser Leu Ser Ser Val Val Thr Val Pro
            420                 425                 430

Ser Ser Ser Leu Gly Thr Gln Thr Tyr Ile Cys Asn Val Asn His Lys
        435                 440                 445

Pro Ser Asn Thr Lys Val Asp Lys Lys Val Glu Pro Lys Ser
    450                 455                 460

<210> SEQ ID NO 4
<211> LENGTH: 557
<212> TYPE: PRT
<213> ORGANISM: Homo sapiens

<400> SEQUENCE: 4

Met Lys Ser Gly Ser Gly Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
            20                  25                  30

Cys Gly Pro Gly Ile Asp Ile Arg Asn Asp Tyr Gln Gln Leu Lys Arg
        35                  40                  45

Leu Glu Asn Cys Thr Val Ile Glu Gly Tyr Leu His Ile Leu Leu Ile
    50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Thr Cys Gly Lys Arg Ala Cys
    210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
        275                 280                 285

Glu Ser Ser Asp Ser Glu Gly Phe Val Ile His Asp Gly Glu Cys Met
    290                 295                 300

Gln Glu Cys Pro Ser Gly Phe Ile Arg Asn Gly Ser Gln Ser Met Tyr
305                 310                 315                 320
```

```
Cys Ile Pro Cys Glu Gly Pro Cys Pro Lys Val Cys Glu Glu Lys
                325                 330                 335
Lys Thr Lys Thr Ile Asp Ser Val Thr Ser Ala Gln Met Leu Gln Gly
            340                 345                 350
Cys Thr Ile Phe Lys Gly Asn Leu Leu Ile Asn Ile Arg Arg Gly Asn
                355                 360                 365
Asn Ile Ala Ser Glu Leu Glu Asn Phe Met Gly Leu Ile Glu Val Val
            370                 375                 380
Thr Gly Tyr Val Lys Ile Arg His Ser His Ala Leu Val Ser Leu Ser
385                 390                 395                 400
Phe Leu Lys Asn Leu Arg Leu Ile Leu Gly Glu Glu Gln Leu Glu Gly
                405                 410                 415
Asn Tyr Ser Phe Tyr Val Leu Asp Asn Gln Asn Leu Gln Gln Leu Trp
            420                 425                 430
Asp Trp Asp His Arg Asn Leu Thr Ile Lys Ala Gly Lys Met Tyr Phe
                435                 440                 445
Ala Phe Asn Pro Lys Leu Cys Val Ser Glu Ile Tyr Arg Met Glu Glu
            450                 455                 460
Val Thr Gly Thr Lys Gly Arg Gln Ser Lys Gly Asp Ile Asn Thr Arg
465                 470                 475                 480
Asn Asn Gly Glu Arg Ala Ser Cys Glu Ser Asp Val Ala Ala Ala Leu
                485                 490                 495
Glu Val Leu Phe Gln Gly Pro Gly Thr His His His His His His Ser
            500                 505                 510
Gly Asp Glu Lys Thr Thr Gly Trp Arg Gly Gly His Val Val Glu Gly
            515                 520                 525
Leu Ala Gly Glu Leu Glu Gln Leu Arg Ala Arg Leu Glu His His Pro
            530                 535                 540
Gln Gly Gln Arg Glu Pro Ser Gly Gly Cys Lys Leu Gly
545                 550                 555

<210> SEQ ID NO 5
<211> LENGTH: 471
<212> TYPE: PRT
<213> ORGANISM: Homo sapiens

<400> SEQUENCE: 5

Met Glu Leu Gly Leu Ser Trp Val Phe Leu Val Ala Ile Leu Glu Gly
1               5                   10                  15
Val Gln Cys Glu Val Gln Leu Val Gln Ser Gly Gly Gly Val Val Gln
            20                  25                  30
Pro Gly Arg Ser Leu Arg Leu Ser Cys Ala Ala Ser Gly Phe Thr Phe
            35                  40                  45
Ser Ser Tyr Gly Met His Trp Val Arg Gln Ala Pro Gly Lys Gly Leu
        50                  55                  60
Glu Trp Val Ser Tyr Ile Ser Ser Ser Gly Ser Thr Ile Tyr Tyr Ala
65                  70                  75                  80
Asp Ser Val Lys Gly Arg Phe Thr Ile Ser Arg Asp Asn Ala Lys Asn
                85                  90                  95
Ser Leu Tyr Leu Gln Met Asn Ser Leu Arg Ala Glu Thr Ala Val
            100                 105                 110
Tyr Tyr Cys Ala Arg Asp Leu Leu Asp Tyr Asp Ile Leu Thr Gly Tyr
            115                 120                 125
Gly Tyr Trp Gly Gln Gly Thr Leu Val Thr Val Ser Ser Ala Ser Thr
        130                 135                 140
```

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
450                 455                 460

Leu Ser Leu Ser Pro Gly Lys
465                 470

<210> SEQ ID NO 6
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Asp Met Arg Val Pro Ala Gln Leu Leu Gly Leu Leu Leu Leu Trp
1               5                   10                  15

Leu Arg Gly Ala Arg Cys Asp Ile Val Met Thr Gln Ser Pro Leu Ser
            20                  25                  30

```
Leu Pro Val Thr Pro Gly Glu Pro Ala Ser Ile Ser Cys Arg Ser Ser
        35                  40                  45

Gln Ser Leu Leu His Ser Asn Gly Tyr Asn Tyr Leu Asp Trp Tyr Leu
 50                      55                  60

Gln Lys Pro Gly Gln Ser Pro Gln Leu Leu Ile Tyr Leu Gly Ser Asn
 65                  70                  75                  80

Arg Ala Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Met Gln Gly Thr His Trp Pro Thr Phe Gly Gln Gly
            115                 120                 125

Thr Lys Leu Glu Ile Lys Arg Thr Val Ala Ala Pro Ser Val Phe Ile
        130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
210                 215                 220

His Gln Gly Leu Ser Ser Pro Val Thr Lys Ser Phe Asn Arg Gly Glu
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
                260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
                340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
        370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
        435                 440                 445
```

```
Met His Glu Ala Leu His Asn His Tyr Thr Gln Lys Ser Leu Ser Leu
            450                 455                 460

Ser Pro Gly Lys
465

<210> SEQ ID NO 7
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Glu Leu Gly Leu Ser Trp Val Phe Leu Val Ala Ile Leu Glu Gly
1               5                   10                  15

Val Gln Cys Glu Val Gln Leu Val Gln Ser Gly Gly Val Val Gln
            20                  25                  30

Pro Gly Arg Ser Leu Arg Leu Ser Cys Ala Ala Ser Gly Phe Thr Phe
            35                  40                  45

Ser Ser Tyr Gly Met His Trp Val Arg Gln Ala Pro Gly Lys Gly Leu
        50                  55                  60

Glu Trp Val Ser Tyr Ile Ser Ser Gly Ser Thr Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Asp Leu Leu Asp Tyr Asp Ile Leu Thr Gly Tyr
        115                 120                 125

Gly Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys

<210> SEQ ID NO 8
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Asp Met Arg Val Pro Ala Gln Leu Leu Gly Leu Leu Leu Leu Trp
1               5                   10                  15

Leu Arg Gly Ala Arg Cys Asp Ile Val Met Thr Gln Ser Pro Leu Ser
            20                  25                  30
```

```
Leu Pro Val Thr Pro Gly Glu Pro Ala Ser Ile Ser Cys Arg Ser Ser
        35                  40                  45

Gln Ser Leu Leu His Ser Asn Gly Tyr Asn Tyr Leu Asp Trp Tyr Leu
 50                      55                  60

Gln Lys Pro Gly Gln Ser Pro Gln Leu Leu Ile Tyr Leu Gly Ser Asn
 65              70                  75                      80

Arg Ala Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Met Gln Gly Thr His Trp Pro Pro Thr Phe Gly Gln Gly
            115                 120                 125

Thr Lys Leu Glu Ile Lys Arg Thr Val Ala Ala Pro Ser Val Phe Ile
        130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
210                 215                 220

His Gln Gly Leu Ser Ser Pro Val Thr Lys Ser Phe Asn Arg Gly Glu
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Val Ala Ala Pro Ser
        355                 360                 365

Val Phe Ile Phe Pro Pro Ser Asp Glu Gln Leu Lys Ser Gly Thr Ala
    370                 375                 380

Ser Val Val Cys Leu Leu Asn Asn Phe Tyr Pro Arg Glu Ala Lys Val
385                 390                 395                 400

Gln Trp Lys Val Asp Asn Ala Leu Gln Ser Gly Asn Ser Gln Glu Ser
                405                 410                 415

Val Thr Glu Gln Asp Ser Lys Asp Ser Thr Tyr Ser Leu Ser Ser Thr
            420                 425                 430

Leu Thr Leu Ser Lys Ala Asp Tyr Glu Lys His Lys Val Tyr Ala Cys
        435                 440                 445
```

```
Glu Val Thr His Gln Gly Leu Ser Ser Pro Val Thr Lys Ser Phe Asn
    450                 455                 460

Arg Gly Glu
465

<210> SEQ ID NO 9
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Asp Met Arg Val Pro Ala Gln Leu Leu Gly Leu Leu Leu Leu Trp
1               5                   10                  15

Leu Arg Gly Ala Arg Cys Asp Ile Val Met Thr Gln Ser Pro Leu Ser
            20                  25                  30

Leu Pro Val Thr Pro Gly Glu Pro Ala Ser Ile Ser Cys Arg Ser Ser
        35                  40                  45

Gln Ser Leu Leu His Ser Asn Gly Tyr Asn Tyr Leu Asp Trp Tyr Leu
    50                  55                  60

Gln Lys Pro Gly Gln Ser Pro Gln Leu Leu Ile Tyr Leu Gly Ser Asn
65                  70                  75                  80

Arg Ala Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Met Gln Gly Thr His Trp Pro Pro Thr Phe Gly Gln Gly
        115                 120                 125

Thr Lys Leu Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335
```

```
Gly Lys Glu Tyr Lys Cys Lys Val Ser Asn Lys Ala Leu Pro Ala Pro
            340             345                 350

Ile Glu Lys Thr Ile Ser Lys Ala Lys Gly Gln Val Ala Ala Pro Ser
        355             360                 365

Val Phe Ile Phe Pro Pro Ser Asp Glu Gln Leu Lys Ser Gly Thr Ala
    370             375             380

Ser Val Val Cys Leu Leu Asn Asn Phe Tyr Pro Arg Glu Ala Lys Val
385             390             395                         400

Gln Trp Lys Val Asp Asn Ala Leu Gln Ser Gly Asn Ser Gln Glu Ser
                405             410             415

Val Thr Glu Gln Asp Ser Lys Asp Ser Thr Tyr Ser Leu Ser Ser Thr
            420             425             430

Leu Thr Leu Ser Lys Ala Asp Tyr Glu Lys His Lys Val Tyr Ala Cys
        435             440             445

Glu Val Thr His Gln Gly Leu Ser Ser Pro Val Thr Lys Ser Phe Asn
    450             455             460

Arg Gly Glu Cys
465
```